United States Patent
Hirsch et al.

(10) Patent No.: US 6,579,536 B1
(45) Date of Patent: Jun. 17, 2003

(54) SUSTAINED-RELEASE PHARMACEUTICAL PREPARATION CONTAINING TILIDINE MESYLATE AS ACTIVE INGREDIENT

(75) Inventors: Richard Hirsch; Martin Wesseling, both of Barleben; Thomas Strungmann, Holzkirchen, all of (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/869,033

(22) PCT Filed: Dec. 23, 1999

(86) PCT No.: PCT/EP99/10381

§ 371 (c)(1),
(2), (4) Date: Jun. 22, 2001

(87) PCT Pub. No.: WO00/38656

PCT Pub. Date: Jul. 6, 2000

(30) Foreign Application Priority Data

Dec. 23, 1998 (DE) .......................... 198 59 636

(51) Int. Cl.$^7$ .............................. A61K 9/14; A61K 9/22
(52) U.S. Cl. ........................ 424/484; 424/486; 424/468
(58) Field of Search ................................. 424/484, 486, 424/468

(56) References Cited

FOREIGN PATENT DOCUMENTS

| EP | 0 864 325 | 9/1998 |
| WO | WO94/10129 | 5/1994 |
| WO | WO99/55662 | 11/1999 |
| WO | WO 99/55662 | * 11/1999 |

* cited by examiner

Primary Examiner—Thurman K. Page
Assistant Examiner—Blessing Fubara
(74) Attorney, Agent, or Firm—Nixon & Vanderhye P.C.

(57) ABSTRACT

The invention relates to a solid, sustained-release pharmaceutical composition for oral administration containing tilidine mesylate as active ingredient.

13 Claims, No Drawings

SUSTAINED-RELEASE PHARMACEUTICAL PREPARATION CONTAINING TILIDINE MESYLATE AS ACTIVE INGREDIENT

The invention relates to a solid sustained-release pharmaceutical composition for oral administration containing tilidine mesylate as an active ingredient.

Tilidine [ethyl-2-(dimethylamino)-1-phenyl-3-cyclohexene-1-carboxylate] represents a synthetic opioid from the group of analgesics having a morphine-like effect. It is used, just like its salts, for treating intense and very intense acute and chronic pain in cases of traumata, post-operative conditions, bone and joint ailments, pain in the region of the thoracic viscera, neuritis, neuralgia, pain caused by tumors, abdominal spasms, painful inflammations, post-traumatic pain, and pain during diagnostic and therapeutic operations.

Tilidine and its salts inhibit the neural transmission of polysynaptic pathways of the nocireceptive system. The effect is mediated through opiate receptors located on the neurons, which also serve as binding sites for naturally occurring peptides, so-called enkephalins.

Tilidine and its salts have only low analgesic activity. The actually active metabolites, nortilidine and bisnortilidine, are formed by metabolization in the liver. The two metabolites are classified as partial morphine antagonists, in that they are very similar to morphine in its pharmacokinetic properties.

Tilidine and many of its pharmaceutically acceptable salts, such as, e.g., tilidine hydrochloride (tilidine-HCl), can be prepared in solid administration forms only under great difficulty or not at all, as the stability of tilidine is very low. Tilidine in combination with solid additives very rapidly decomposes during manufacture and storage, which is indicated by discoloration. In addition, many of the tilidine salts are found to be highly hygroscopic and thus difficult to process.

Due to its stability, the tilidine dihydrogen orthophosphate described in patent specification EP 0 665 830 B1 represents the tilidine salt commonly used for the preparation of solid drugs. Manufacture of this salt, however, requires high safety standards, as quite specific conditions must be maintained in order to avoid critical situations.

It has now been found that tilidine mesylate has a sufficiently high stability and thus is very suitable for the preparation of solid drugs as it virtually does not undergo any decomposition in the solid form, i.e. in combination with solid additives. Furthermore, the high stability ensures easy processing, as there are no particular requirements to air conditioning of the work rooms and to corrosion protection of the equipment and instruments used. The preparation of tilidine mesylate may thus be carried out without any particular safety measures while using conventional laboratory equipment.

Although therapy with rapid-release drugs attempts to maintain long lasting therapeutically effective blood plasma levels of the active ingredient by frequent and at the same time regular administration of the active ingredient, the blood plasma level nevertheless varies considerably due to the instantaneous absorption, systemic excretion, and hepatic metabolization of the active ingredient. As a result, the effectivity of the active ingredient may be strongly impaired.

Considering the above, the object of the present invention is to provide a solid sustained-release pharmaceutical composition for oral administration containing tilidine mesylate as an active ingredient, so that patient compliance is improved through a reduced frequency of administration, and the effectivity of the active ingredient is optimized.

In the present context, "sustained-release" is to be understood as a release rate of the active ingredient wherein a therapeutically effective blood plasma level is achieved over a period of at least 8–12 hours and optionally of up to 24 hours. A therapeutically effective blood plasma level in particular is within the range of from 30 to 50 ng/ml of nortilidine.

It has been found that by means of the composition according to the invention a steady blood plasma level may be ensured over a period of at least 8 to 12 hours and optionally of up to 24 hours. The frequency of administration may thus be reduced to one or two doses per day.

The composition according to the invention contains an analgesically effective amount of tilidine mesylate per dosage unit corresponding to an amount of 50–500 mg of tilidine hydrochloride (tilidine-HCl), with the preferred dosage units containing an amount of tilidine mesylate corresponding to 50 mg, 100 mg, 150 mg and 200 mg of tilidine-HCl.

The composition according to the invention may be in the form of granulates, pellets, spheroids and/or extrudates. These may either be filled into capsules or sachets or pressed to form tablets. Moreover, the active ingredient and possible additives may optionally be tabletted directly.

The active ingredient used in the composition according to the invention, tilidine mesylate, may be embedded in a matrix. This matrix ensures the sustained release of tilidine mesylate over a period of at least 8 to 12 hours and optionally of up to 24 hours (matrix-controlled).

Suitable matrix-forming materials:

a) Hydrophilic or hydrophobic polymers, such as, e.g., gums, cellulose ethers, cellulose esters, acrylic resins, protein-based materials, nylon, polyvinyl chloride, starch and/or polyvinyl pyrrolidone. Suitable water-soluble polymers are, i.a., polyvinyl pyrrolidone, hydroxypropyl cellulose, hydroxypropylmethyl cellulose, hydroxyethyl cellulose, hydroxymethyl cellulose, poly(vinyl alcohols), alginates, polydextrose, carboxymethylene, hydrogenated hydroxyalkyl cellulose and/or hydroxypropylmethyl cellulose ether. As water-insoluble polymers polyvinyl chloride, ethyl cellulose, methyl cellulose, carboxymethyl cellulose (partly water-soluble, depending on the average degree of substitution), cellulose acetates, cellulose acetate phthalates, ethylene vinyl alcohol, alginic acid and/or its derivatives, acrylic acid and/or methacrylic acid copolymers, methyl methacrylate copolymers, ethoxy ethyl methacrylate copolymers, cyanoethyl methacrylates, aminoalkyl methacrylate copolymers, poly(acrylic acid), poly(methacrylic acid), methacrylic acid alkylamide copolymers, poly(methyl methacrylates), poly(methacrylic anhydrides), methyl methacrylates, polymethacrylates, poly(methyl methacrylate) copolymer, polyacrylamides, aminoalkyl methacrylate copolymers and/or glycidyl methacrylate copolymers may be used. The composition according to the invention may contain 1–90% (weight percent) of one or more of the hydrophilic or hydrophobic polymers as a matrix.

b) Digestible, substituted or unsubstituted long-chain ($C_8$–$C_{50}$, in particular $C_{12}$–$C_{40}$) hydrocarbons such as, e.g., fatty acids, fatty alcohols (lauryl, myristyl, stearyl, cetostearyl, ceryl or cetyl alcohol), glycerol esters of fatty acids (Witepsol, glycerol monostearate), mineral and vegetable oils (hydrogenated castor oil) and/or waxes (paraffin waxes, silicone waxes, beeswaxes, castor waxes, carnauba waxes and/or Glyco waxes). The hydrocarbons having a melting point between 25° C. and 90° C. are particularly useful. Preferred long-chain hydrocarbons are fatty alcohols. The composition according to the invention may contain at least one of the digestible, long-chain hydrocarbons, wherein their content may be up to 60% (weight percent), based on the matrix.

c) Polyalkylene glycols, wherein the composition according to the invention may contain up to 60% (weight percent) of one or more polyalkylene glycols, based on the matrix.

The preferred matrix form according to the invention may contain the active ingredient, tilidine mesylate, in a gel-forming matrix of, e.g., hydroxymethyl cellulose, hydroxyethyl cellulose, hydroxypropyl cellulose, hydroxypropylmethyl cellulose, alginate and/or polyacrylic acid, in particular hydroxypropylmethyl cellulose. The polymer hydrates to form a gel-like layer, i.e., a hydrogel matrix that slowly releases the active ingredient in a controlled manner by way of diffusion and erosion.

In another matrix form according to the invention, the active ingredient, tilidine mesylate, may be combined with known water-soluble additives and fatlike substances. As lipophilic substances degradable mono-, di- and triglycerides (glycerol monostearate, glycerol monooleate, glycerol tripalmitate), but also erodable fatty alcohols (lauric, myristic, stearic, cetylic and/or ceryl alcohol) having a melting point in the range of from 30–80° C. may be used. Delivery of the active ingredient takes place by diffusion and by enzymatic degradation of the lipophilic substances. Embedding of the active ingredient into the matrix is achieved by melting, spray solidification, spray-drying, granulating or direct tabletting.

A further useful sustained-release matrix form may contain, in addition to the active ingredient tilidine mesylate, known water-soluble additives which are embedded, just like the active ingredient, in a framework structure formed of water-insoluble, indigestible additives. Elution of the soluble constituents generates pores through which the active ingredient diffuses to the outside. Polymers such as polyvinyl chloride, polyethylene, polyamide, silicones, ethyl cellulose and/or methacrylate-acrylate copolymers may be employed as structure-building substances. The mixture of active ingredient/additive is either immediately pressed to form tablets or following wet granulation with organic solvents or binder solutions, or it is filled into capsules in pellet form.

Such a sustained-release matrix may consist of one or more alkyl celluloses and one or more aliphatic $C_{12}$–$C_{36}$ alcohols and, optionally, at least one polyalkylene glycol. Preferably, a $C_1$–$C_6$ alkyl cellulose is used, in particular ethyl cellulose. The content of alkyl celluloses in the matrix may be in the range of from 1–20% (weight percent), in particular 2–15% (weight percent).

Useful aliphatic alcohols are lauryl, myristyl, stearyl, cetostearyl, ceryl and/or cetyl alcohol. The content of aliphatic alcohols in the matrix may be in the range of from 5–30% (weight percent), in particular 10–25% (weight percent).

Preferably, polyethylene glycol is used as the polyalkylene glycol component.

The sustained-release matrix may contain further pharmaceutically useful additives which are conventional according to the prior art, such as, e.g., diluents, lubricants, binders, granulation aids, colorants, flavoring agents, detergents, buffers, antiblocking agents and/or lubricating agents.

The composition embedded in a sustained-release matrix according to the invention may moreover be film-coated with a known, pharmaceutically acceptable surface coating without sustained-release properties. Aqueous film coatings as available, for example, under the trade name Opadry®, are preferred.

Another embodiment of the invention may consist of an initial dose and a delayed-release component. The initial dose contains tilidine mesylate as a powder, granulate and/or pellets, optionally together with respective additives. The tilidine mesylate contained in the initial dose is released immediately following administration. The therapeutically effective blood plasma level is attained very rapidly by means of this initial dose, so that a therapeutic effect is observed shortly after administration. The delayed-release component contains tilidine mesylate as a granulate and/or pellets, optionally together with respective additives. This delayed-release component accounts for the maintenance of a therapeutically effective blood plasma level over several hours. Thus, a blood plasma level which is uniformly high over several hours may be ensured for the patient. The granulate or the pellets may contain retarding additives which form a sustained-release matrix. As suitable substances forming a sustained-release matrix, the above mentioned matrix-forming materials may be used.

The preparation according to the invention may be present in the form of a two-layer tablet. The first layer represents the initial dose which is pressed from powder and, optionally, additives, the above described granulate and/or pellets. The second layer contains the above described delayed-release component which is pressed from the corresponding granulate and/or pellets.

The tilidine mesylate content in the initial dose may amount to 5–30 wt. % of the total tilidine mesylate content.

For the preparation of the above mentioned dosage forms, the pharmaceutical additives known from the prior art may be used, such as tablet binders, fillers, preservatives, tablet disintegrants, flow regulating agents, plasticizers, wetting agents, dispersing agents, emulsifiers, retarding agents, antioxidants and/or other known carrier substances and diluents.

In addition to tilidine mesylate, the composition according to the invention may optionally contain the opiate antagonist naloxone. Naloxone prevents abuse by heroin addicts and reduces the risk of addiction. The composition may further contain citric acid, ascorbic acid and/or derivatives thereof, sulfur dioxide, sodium sulfite, sodium bisulfite and/or tocopherol as well as its water- and fat soluble derivatives, for example those available under the trade name Tocofersolan® or tocopherol acetate, sulfites, bisulfites and/or hydrogen sulfites of alkali, alkaline earth and/or other metals, PHB esters, BHA, BHT, gallates as well as lower fatty acids, fruit acids, phosphoric acids, sorbic and/or benzoic acid as well as the salts, esters, derivatives and/or isomeric compounds thereof, ascorbylpalmitate, lecithin, mono- and polyhydroxylated benzene derivatives, ethylenediaminetetraacetic acid and/or the salts thereof, citraconic acid, cysteine, L-cysteine, conidendrins, diethyl carbonates, methylene dioxyphenols, cephalins, β,β'-dithiopropionic acid, biphenyl and/or other phenyl derivatives, which may serve to stabilize the composition.

The in-vitro release rate of the composition according to the invention is 5–50%, preferably 10–40% (weight percent) tilidine mesylate after one hour; 10–75%, preferably 20–50% (weight percent) tilidine mesylate after two hours; 20–95%, preferably 30–80% (weight percent) tilidine mesylate after four hours; 40–100%, preferably 50–100% (weight percent) tilidine mesylate after eight hours; more than 50%, preferably more than 60% (weight percent) tilidine mesylate after twelve hours; more than 70%, preferably more than 80% (weight percent) tilidine mesylate after eighteen hours; and more than 80%, preferably more than 90% (weight percent) tilidine mesylate after twenty-four hours, preferably as determined in accordance with USP, Basket Method, in 1000 ml of 0.1 M HCl.

Furthermore, in the case of the composition according to the invention, after eight hours at least 70–95% (weight percent) tilidine mesylate, after ten hours at least 77–97% (weight percent) tilidine mesylate, and after twelve hours at least 80–100% tilidine mesylate are absorbed in vivo.

The invention is further illustrated by the following examples without limiting the scope of invention.

EXAMPLE 1

| Components | mg/tablet |
| --- | --- |
| Tilidine mesylate (anhydrous) | 120.00 |
| Naloxone-HCl × 2 H$_2$O | 8.80 |
| Mixture of lactose and microcrystalline cellulose (Microcellac 100) | 350.00 |
| Polyvinyl pyrrolidone (Kollidon ® 25) | 50.00 |
| Cellulose ether (Metolose 90 SH 100000) | 50.00 |
| Silicon dioxide (Aerosil) | 2.00 |
| Magnesium stearate | 2.00 |

Components 1 to 6 are sieved and mixed intimately. Magnesium stearate is also sieved and admixed to the mixture of components 1 to 6. The composition is tabletted directly. After pressing, the tablet core (total weight: 582.8 mg) is coated with an aqueous film (Opadry®). The film thickness is variable.

EXAMPLE 2

The following substances are used for the preparation of 1,000 tablets [total weight 253.64 mg, 59.64 mg of tilidine mesylate (corresponding to 50 mg of tilidine-HCl or 44.12 mg of tilidine)].

| Components | Percent | Weight (g) |
| --- | --- | --- |
| Tilidine mesylate | 23.5 | 59.64 |
| Naloxone-HCl | 1.6 | 4 |
| Mannitol | 19.6 | 50 |
| Lactose, anhydrous | 13.8 | 35 |
| Hydroxyethyl cellulose (Natrosol ® 250 HX) | 10.5 | 26.6 |
| Hydroxypropyl cellulose (Klucel ® HF) | 10 | 25 |
| Cetostearyl alcohol | 21 | 53.4 |

Tilidine mesylate, naloxone-HCl, mannitol, lactose, hydroxyethyl cellulose and hydroxypropyl cellulose (15 g as a binder) are dry-mixed. The mixture is then wetted with 439 g of water until a wet granulating mass is obtained. The wetted mixture is allowed to begin to dry slightly in a Fluid Bed Dryer (FBD) at 60° C. and then is granulated and passed through a mesh 12 screen. Subsequently the granulate is dried completely in an FBD at 60° C., regranulated and passed through a 1.25-mm screen (mesh 16). Molten cetyl-stearyl alcohol is added to the warm tilidine mesylate granulate followed by thorough mixing. The mixture is cooled in an air current, regranulated, and passed through a 1.25-mm screen.

The remaining hydroxypropyl cellulose (10 g) is added to the mixture and mixed with the granulate until the granulate has a sufficiently thick coating of hydroxypropyl cellulose. Subsequently the granulate is pressed to form tablets. If desired, the tablets may be further coated with standard coatings.

EXAMPLE 3

| Components | Weight in grams |
| --- | --- |
| Tilidine mesylate | 119.27 |
| Carboxymethyl cellulose | 135 |
| Sodium dioctyl sulfosuccinate (Ultrawet 40DS) | 7.5 |
| Talc | 2.5 |
| Magnesium stearate | 1.5 |
| Lactose | 53.75 |

Sodium dioctyl sulfosuccinate is dissolved in isopropanol. Carboxymethyl cellulose is mixed with this solution until the mixture is homogeneous. The mixture is then granulated and passed through a mesh 16 screen. The granulate is dried in an air current until complete evaporation of the isopropanol. Tilidine mesylate and lactose are added and mixed. Subsequently magnesium stearate and talc are admixed and mixing is performed until the mixture is homogeneous. The mixture is then regranulated and passed through a mesh 16 screen. The obtained granulate is pressed to form tablets or filled into capsules or sachets. The amount of tilidine mesylate per capsule, tablet or sachet is 119.27 mg, corresponding to 100 mg of tilidine-HCl and 88.24 mg of tilidine. 1,000 units each having a total weight of 319.52 mg are prepared.

EXAMPLE 4

| Components | Weight in grams |
| --- | --- |
| Tilidine mesylate | 119.27 |
| Naloxone-HCl | 8 |
| Polydextrose | 20 |
| Hydrogenated castor oil | 15 |
| Cetostearyl alcohol | 35 |
| Talc | 3 |
| Magnesium stearate | 1 |

Tilidine mesylate, naloxone-HCl and hydrogenated castor oil are granulated with polydextrose, and the granulate is passed through a 1.25-mm screen and dried at 60° C. in an FBD. Molten cetostearyl alcohol is added to this granulate. This mixture is cooled an in air current and again passed through a 1.25-mm screen. Talc and magnesium stearate are mixed with the granulate and then either pressed to form tablets or filled into capsules and sachets. This batch yields 1,000 units having a total weight of 201.07 mg/unit. Each tablet, capsule or sachet contains 119.27 mg of tilidine mesylate, corresponding to 100 mg of tilidine-HCl and 88.24 mg of tilidine.

EXAMPLE 5

| Components | Weight in mg/dosage unit |
| --- | --- |
| Tilidine mesylate | 119.27 (corresponding to 100 mg of tilidine-HCl) |
| Polyvinyl pyrrolidone | 3.4 |

-continued

| Components | Weight in mg/dosage unit |
|---|---|
| Acrylic resin (Eudragit ® RS) | 20 |
| Acetone/isopropanol | q.s. |
| Cetostearyl alcohol | 66.6 |
| Magnesium stearate | 2.4 |
| Talc | 6 |

Tilidine mesylate and polyvinyl pyrrolidone (PVP) are mixed rapidly in an appropriate apparatus. Eudragit® is dissolved in acetone/isopropanol (50:50) (granulating fluid). During mixing of the tilidine mesylate and the PVP this granulating fluid is slowly added until a wet granulation mass is formed. The resulting granulate is then dried and passed through a mesh 12 screen. The cetostearyl alcohol, melted at a temperature of 60–70° C., is added to the still-warm granulate followed by mixing. After cooling the granulate is passed through a 1.7-mm screen. Subsequently the talc and the magnesium stearate are admixed followed by mixing. The granulate is either pressed to form tablets or filled into capsules or sachets.

EXAMPLE 6

Natural gum (SMR 20 NR, 1 g) is dissolved in toluene (100 ml) with refluxing over 24 hours. The resulting slightly yellow solution is cooled and the small proportion of undissolved gum is sedimented. This sedimentation step may be accelerated by centrifugation. 12 ml of this clear solution are diluted with 10 ml of toluene and used for the further preparation step.

Tilidine mesylate (3.05 g), magnesium stearate (0.58 g), cellulose powder (0.44 g) and ethylene-vinyl acetate copolymer (Vinnapas RE 530Z, 5.81 g) are mixed and homogenized. This mixture is ground with the above described solution. A wet suspension is obtained. The latter is dried under vacuum, accompanied by frequent grinding. The matrix thus obtained may be employed directly for tabletting.

EXAMPLE 7

238.54 g of tilidine mesylate and 16 g of naloxone-HCl are mixed with 40 g of ethyl cellulose and 25 g of polyvinyl pyrrolidone. 140 g of lactose and 203 g of talc are added, wetted with a sufficient quantity of alcohol and granulated followed by drying. The obtained granulate is either pressed to form tablets or filled into capsules. The dosage unit prepared in this way contains 238.54 mg of tilidine mesylate (corresponding to 200 mg of tilidine-HCl and to 176.5 mg of tilidine).

EXAMPLE 8

| Components | mg/tablet |
|---|---|
| Tilidine mesylate (anhydrous) | 120.00 |
| Naloxone-HCl × 2 H$_2$O | 8.00 |
| Lactose | 308.00 |
| Polyvinyl pyrrolidone | 50.00 |
| Hydroxypropylmethyl cellulose | 185.00 |
| Water, purified (to be removed) | 185.00 |
| Magnesium stearate | 6.00 |

A granulate was prepared as described in Example 7 and was pressed after drying to form tablets.

EXAMPLE 9

| Components | Quantity/unit |
|---|---|
| Two-layer tablet: | |
| Initial dose: | |
| Tilidine mesylate | 29.81 mg (corresponding to 25 mg of tilidine-HCl) |
| Naloxone-HCl | 2 mg |
| Lactose | 15 mg |
| Dicalcium phosphate dihydrate | 20 mg |
| microcrystalline cellulose | 24.5 mg |
| Sodium carboxymethyl cellulose | 4 mg |
| Magnesium stearate | 1 mg |
| Aerosil 200 | 0.5 mg |
| Sustained-release dose: | |
| Tilidine mesylate | 149.1 mg (corresponding to 125 mg of tilidine-HCl) |
| Naloxone-HCl | 10 mg |
| Lactose D20 | 128.5 mg |
| Metolose ® 90 Sh-100000 | 50 mg |
| Kollidon ® 25 | 5 mg |
| Green lacquer | 25 mg |
| Water | 5.4 µl |
| Magnesium stearate | 3.75 mg |
| Aerosil 200 | 3.5 mg |

Preparation of the Sustained-Release Granulate

Kollidon® is dissolved in water and the green lacquer is dispersed therein. Tilidine mesylate, naloxone-HCl, lactose and Metolose® are placed in a fluidization granulator and granulated with the previously prepared solution. Magnesium stearate and Aerosil are added to the obtained granulate and passed through a 1.0-mm screen and homogenized in a container mixer.

Preparation of the Initial Dose

All the ingredients of the initial dose are passed through a 0.8-mm screen and are homogenized in a container mixer.

The sustained-release granulate is pressed, together with the initial dose, on a suitable rotary pelleter to form the two-layer tablets.

What is claimed is:

1. Solid pharmaceutical composition for oral administration having a sustained-release matrix, containing tilidine mesylate as an active ingredient.

2. Solid pharmaceutical composition for oral administration having a sustained-release matrix according to claim 1, wherein tilidine mesylate is present in an amount equivalent to an amount of 50–500 mg of tilidine-HCl.

3. Solid pharmaceutical composition for oral administration having a sustained-release matrix according to claim 1, wherein said sustained-release matrix contains as retardation agents hydrophilic and/or hydrophobic polymers.

4. Solid pharmaceutical composition for oral administration having a sustained-release matrix according to claim 1 in the form of powder, granulate, pellets, spheroids and/or extrudates, which can be filled into capsules or sachets or pressed to form tablets.

5. Solid pharmaceutical composition for oral administration having a sustained-release matrix according to claim 1, comprising the following components:

i) an initial dose of active ingredient containing a therapeutically effective amount of tilidine mesylate as an active ingredient and, optionally, additives;

ii) a delayed-release component containing a therapeutically effective amount of tilidine mesylate as an active ingredient and, optionally, additives.

6. Solid, pharmaceutical composition for oral administration having a sustained-release matrix according to claim 5 in the form of a two-layer tablet, wherein the first layer consists of the initial dose and the second layer consists of the delayed-release component.

7. Solid, sustained release pharmaceutical composition for oral administration according to claim 1, wherein said composition contains tablet binders, fillers, preservatives, tablet disintegrants, flow regulating agents, lubricants, plasticizers, wetting agents, dispersing agents, emulsifiers, retarding agents, binders, granulation aids, coloring agents, flavoring agents, detergents, buffers, antiblocking agents, lubricating agents, antioxidants and/or carriers and diluents as additives.

8. Solid, sustained-release pharmaceutical composition for oral administration according to claim 1, wherein said composition comprises a combination of the active ingredient tilidine mesylate with naloxone and/or pharmaceutically acceptable salts thereof.

9. Solid pharmaceutical composition of claim 2, wherein tilidine mesylate is present in an amount equivalent to an amount of 50 mg of tilidine-HCl.

10. Solid pharmaceutical composition of claim 2, wherein tilidine mesylate is present in an amount equivalent to an amount of 100 mg of tilidine-HCl.

11. Solid pharmaceutical composition of claim 2, wherein tilidine mesylate is present in an amount equivalent to an amount of 150 mg of tilidine-HCl.

12. Solid pharmaceutical composition of claim 2, wherein tilidine mesylate is present in an amount equivalent to an amount of 200 mg of tilidine-HCl.

13. Solid pharmaceutical composition for oral administration having a sustained-release matrix according to claim 3, wherein said polymers are selected from the group consisting of gums, cellulose ethers, cellulose esters, protein-based materials, nylon, polyvinyl chloride, starch, polyvinyl pyrrolidone, alginates, polydextrose, carboxymethylene, acrylic resins, poly(vinyl alcohols), ethylene vinyl alcohol, alginic acid and/or derivatives thereof, and/or fatty acids, fatty alcohols, glycerol esters of fatty acids, mineral and vegetable oils, waxes and/or polyalkylene glycols.

* * * * *